(12) United States Patent
Roe

(10) Patent No.: US 6,645,219 B2
(45) Date of Patent: Nov. 11, 2003

(54) ROTATABLE PENETRATION DEPTH ADJUSTING ARRANGEMENT

(75) Inventor: Steven N. Roe, San Mateo, CA (US)

(73) Assignee: Amira Medical, Indianapolis, IN (US)

( * ) Notice: Subject to any disclaimer, the term of this patent is extended or adjusted under 35 U.S.C. 154(b) by 0 days.

(21) Appl. No.: 09/948,064

(22) Filed: Sep. 7, 2001

(65) Prior Publication Data

US 2003/0050655 A1 Mar. 13, 2003

(51) Int. Cl.[7] .............................................. A61B 17/32
(52) U.S. Cl. ........................................ 606/182; 606/172
(58) Field of Search ................................ 606/172, 182, 606/183, 181

(56) References Cited

U.S. PATENT DOCUMENTS

| | | | | |
|---|---|---|---|---|
| RE32,922 E | * | 5/1989 | Levin et al. | 128/314 |
| 4,895,147 A | * | 1/1990 | Bodicky et al. | 606/182 |
| 5,318,584 A | * | 6/1994 | Lange et al. | 606/182 |
| 5,439,005 A | * | 8/1995 | Vaughn | 600/568 |
| 5,730,753 A | * | 3/1998 | Morita | 606/181 |
| 5,879,311 A | | 3/1999 | Duchon et al. | |
| 5,951,492 A | * | 9/1999 | Douglas et al. | 600/583 |
| 5,951,493 A | * | 9/1999 | Douglas et al. | 600/583 |
| 5,964,718 A | | 10/1999 | Duchon et al. | |
| 6,022,366 A | * | 2/2000 | Schraga | 606/181 |
| 6,048,352 A | * | 4/2000 | Douglas et al. | 606/181 |
| 6,071,250 A | * | 6/2000 | Douglas et al. | 600/583 |
| 6,319,210 B1 | * | 11/2001 | Douglas et al. | 600/583 |
| 6,464,649 B1 | * | 10/2002 | Duchon et al. | 600/583 |
| 2001/0011157 A1 | * | 8/2001 | Latterell et al. | 600/576 |
| 2002/0169470 A1 | * | 11/2002 | Kuhr et al. | 606/182 |

FOREIGN PATENT DOCUMENTS

EP 0931507 A1 7/1999

* cited by examiner

*Primary Examiner*—Michael J. Milano
*Assistant Examiner*—Bradford C Pantuck
(74) *Attorney, Agent, or Firm*—Woodard, Emhardt, Moriarty, McNett & Henry LLP

(57) ABSTRACT

An arrangement of interfitting components for adjusting the penetration depth of a lancet and for stimulating an area surrounding an incision formed by penetration of a surface of the skin by the lancet, thereby facilitating the extraction of a sample of bodily fluid with a minimally invasive incision, the arrangement includes: a bottom end adapted to be applied to the surface of the skin, and a top end opposite the bottom end; a longitudinally moveable lancing member having a sharp end; a stop member setting a longitudinal travel distance of the lancing member; a bottom surface adapted to be applied to the surface of the skin, and an opening in the bottom surface through which the lancing member projects; a penetration depth defined by the distance between the end of the lancing device and the bottom surface; an adjusting mechanism for changing the penetration depth; and a stimulation mechanism for stimulating the area surrounding the incision and facilitating the extraction of the sample of bodily fluid.

26 Claims, 12 Drawing Sheets

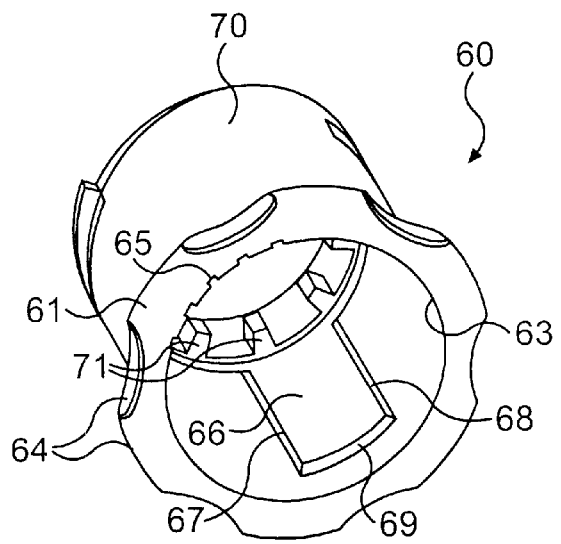
FIG. 8A
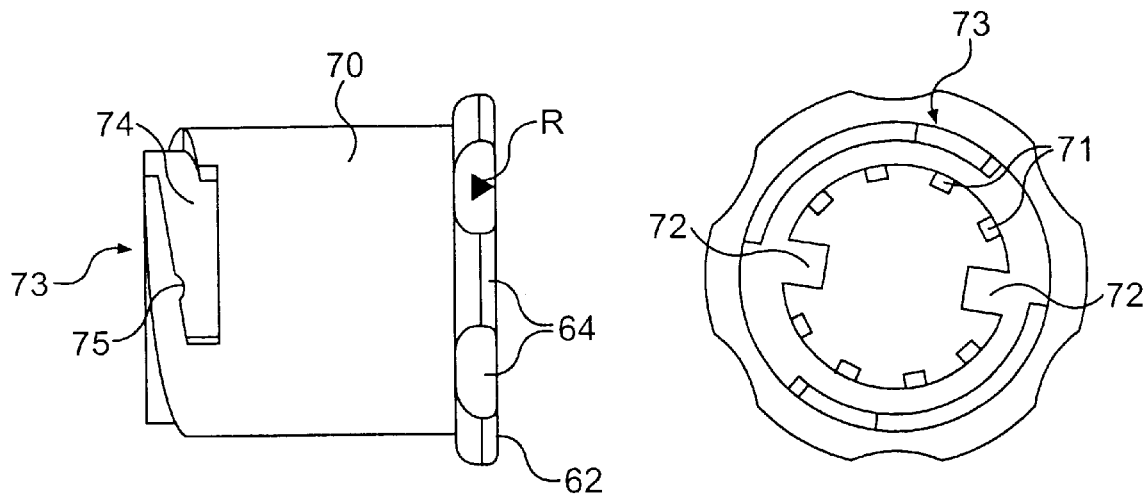
FIG. 8B
FIG. 8C

ROTATABLE PENETRATION DEPTH ADJUSTING ARRANGEMENT

FIELD OF THE INVENTION

The present invention relates to an adjustable assembly. More particularly, the present invention relates to an adjustable assembly especially suited for use in a body fluid sampling device.

BACKGROUND OF THE INVENTION

In the description of the background of the present invention that follows reference is made to certain structures and methods, however, such references should not be construed as an admission that these structures and methods qualify as prior art under the applicable statutory provisions. Applicants reserve the right to demonstrate that any of the referenced subject matter does not constitute prior art with regard to the present invention.

Many medical procedures in use today require a relatively small sample of bodily fluid. The term bodily fluid is intended primarily to encompass blood, interstitial fluid, or a mixture of the two, however, the term could also include urine, saliva, etc. Such samples are often obtained by lancing or piercing the skin at a selected location, such as the finger, to enable the collection of 1 or 2 drops of blood.

With the advent of home use tests such as self monitoring of blood glucose, there is a requirement for a simple, reliable procedure which can be performed in any setting by a person needing to test, and which minimizes discomfort to the person being sampled and tested.

Lancets in conventional use generally have a rigid body and a sterile needle which protrudes from one end. The lancet may be used to pierce the skin, thereby enabling the collection of a sample from the opening created. Blood is commonly taken from the fingertips, where the supply is generally excellent. The nerve density in this region causes significant pain in many patients. Repeated lancing of the fingertips results in callous formation. This leads to increased difficulty in drawing blood and increased pain.

Sampling of alternate site, such as earlobes and limbs, is sometimes practiced to access sites which are less sensitive. However, obtaining an adequate sample, and transferring the sample to a test strip or reading device, from such non-fingertip locations often proves to be difficult.

To reduce the anxiety of piercing the skin and the associated pain, many spring loaded devices have been developed. U.S. Pat. No. 4,503,856 to Cornell et al. and U.S. Pat. No. 4,517,978 to Levin et al. are representative of the devices which were developed in the 1980's for use with home diagnostic test products, the disclosures of which are incorporated herein by reference in their entirety. Even with the large amount of activity and development in this area, many conventional devices have undesirable aspects.

U.S. Pat. Nos. 5,879,311; 5,857,983; 6,048,352; 5,951,492; 5,951,493; 5,964,718; and 6,086,545 represent important advance(s) in this area. The disclosures of these patents are incorporated herein by reference, in their entirety. Through the constructions and methods set forth in these patents, adequate samples of bodily fluid are reliably obtained, even from non-fingertip locations, in a minimally invasive and substantially pain-free manner.

At least some of the above-mentioned U.S. Patents involve applying a skin-lancing medium against a skin surface to form an incision therein, removing the skin-lancing medium from the incision, and thereafter applying a force to depress the skin in a manner forming a ring of depressed body tissue in surrounding relationship to the incision, causing the incision to bulge and the sides of the incision to open, whereby bodily fluid is forced out through the opening of the incision. This enables an adequate and adjustable sample size to be obtained, even from areas of the body in which the blood supply is less plentiful, with a minimally invasive lancing procedure.

In this regard, the sampling device can include having a housing with a lower end. At the lower end of the housing a stimulator mechanism is provided which is relatively movable with respect to the housing and which has an end face adapted to engage the skin surface and bulge open the lanced opening in response to being pressed one or more times against the skin surface. This construction facilitates the extraction of the bodily fluid, thereby enabling an adequate sample to be obtained from a relatively small lanced incision in the skin surface and reducing the pain associated with such techniques.

While the above-mentioned construction is clearly advantageous, it would also be beneficial to provide such a construction and technique with a simple, user-friendly and reliable way to adjust the depth of penetration of the lancet into the surface of the skin.

The are numerous known devices which per se provide an adjustable depth of penetration of a lancet into the surface of the skin.

U.S. Pat. No. 4,895,147 to Bodicky et al. discloses a lancet injector which includes an elongate tubular housing, and a penetration depth selector disposed thereon. The rotatable depth selector includes a number of variable depth contact edges. These contact edges present a jagged surface which is exposed on the outside of the housing. This construction is undesirable, since such exposed jagged edges could pose a safety concern, and do not present an aesthetically pleasing form. The aesthetics of such devices are of particular importance since the users are already apprehensive due to the traditionally painful nature of the testing procedure. Thus, a relatively more aesthetically pleasing design will reduce such apprehension and encourage more frequent use which is important in situations such as the self-monitoring of blood glucose content. Moreover, Bodicky et al. does not disclose a device including a stimulator mechanism which is relatively movable with respect to the housing. Thus, the device of Bodicky et al. is not as effective in extracting an adequate sample of bodily fluids, especially from non-fingertip locations.

U.S. Pat. No. 6,022,366 to Schraga discloses a lancet device including an adjustable penetration depth mechanism. In one embodiment, Schraga discloses a device wherein the penetration depth is adjusted by adjusting the length of the needle holding member. According to this embodiment, a proximal segment is rotated relative to a cental segment, thereby increasing or decreasing the overall length of the needle holding member. During rotation, a protruding element snaps into and out of grooves provided on the inner diameter of the proximal segment. However, such a construction provides for a relatively limited number of adjustments because only a limited number of grooves can be disposed upon the inner diameter of the proximal segment, due to the relatively small size typical in such devices. Moreover, the device described by Schraga requires that the user remove the cap member in order to adjust the penetration depth, then the cap member must be replaced by the user after the adjustment has been made. This construction is obviously inconvenient to the user, adds an extra degree of difficulty to the operation of the device, and could pose a safety hazard due to the potential exposure of the user to the sharp lancet needle during the adjustment process. Moreover, the device of Schraga does not include a stimulator mechanism, or a stimulator mechanism which is relatively movable with respect to the housing. Thus, the device of Schraga lacks the desirable degree of effectiveness in extracting an adequate sample from non-fingertip locations, particularly with a minimally invasive lancing procedure.

U.S. Pat. No. 5,613,978 to Harding discloses an adjustable tip for a blood lancet device for causing different depths of skin puncture. The device of Harding includes an inner sleeve and a partially enclosed distal end which forms a stop for the shoulder of the lancet. Rotation of an outer sleeve causes longitudinal motion between the distal ends of the inner sleeve and outer sleeve, thereby creating an adjustable double bottom which creates various puncture depths. However, the device of Harding is for fingertip sampling. Nowhere does Harding disclose, or even suggest, that a device having the construction described therein is suitable for non-fingertip sampling. Moreover, the device of Harding lacks a stimulator member, much less a stimulator member which is relatively movable with respect to the housing. Thus, the device of Harding is not suitable for minimally invasive sampling, particularly at non-fingertip locations.

U.S. Pat. No. 6,045,567 to Taylor et al. discloses a lancing device having a spring-loaded lancet holder slidably mounted within a housing. The device is further provided with a knob on the back of the device which includes forwardly extending fingers that act to stop the lancet holder at an adjustable predetermined point after the device has been fired. Thus, the fingers act to control the penetration depth of the needle. However, the device of Taylor et al. is specifically constructed for fingertip sampling. Nowhere does Taylor et al. mention, or even suggest that the device constructed as described therein is suitable for non-fingertip sampling. Moreover, the device of Taylor et al. lacks a stimulator member, or a stimulator member which is relatively movable with respect to the housing. Thus, the device of Taylor et al. is not suitably constructed for non-fingertip minimally invasive sampling.

U.S. Pat. No. 5,730,753 to Morita describes an assembly which comprises a cap element for mounting onto an injector. The cap has a stop which is constructed such that an end of the lancet from which the lancing member protrudes abuts against the stop during operation of the device. The device further includes an adjusting element which engages the cap, as well as a cover element between these elements. The distance between the stop and an opening along a direction of the lancet movement is changed by rotating the adjusting element around an axis of rotation of the lancet ejector. However, the device described by Morita is heavily dependent upon the elasticity of the material which makes up the various components. Thus, this construction is more readily prone to failure, due to failure of the material from which it is constructed. This is particularly important since it is beneficial to construct such devices of relatively inexpensive materials in order to reduce cost to the consumer. The device of Morita is specifically constructed for application in finger stick devices. Thus, Morita give no indication that the device described therein would be suitable for minimally invasive sampling and non-fingertip locations. Moreover, the device of Morita does not include a stimulator member, or a stimulator member which is relatively movable with respect to the housing thereof.

Thus, it would be desirable to provide an improved assembly which enables the penetration depth of a lancing member to be adjusted in a simple yet effective and reliable manner, particularly in devices which are constructed for the sampling of bodily fluids in non-fingertip locations, with a minimally invasive lancing procedure.

SUMMARY OF THE INVENTION

It is an object of the present invention to provide an adjustable assembly which overcomes the problems associated with the prior art.

According to one aspect, the present invention provides an adjustable arrangement comprising a carrier; a guide tube, the guide tube receiving the carrier in a longitudinally slidable manner, the guide tube comprises a stop member limiting longitudinal movement of the carrier; an inner ring, the inner ring adjustably attached to the guide tube, the inner ring comprising a bottom surface adapted to contact a surface of the skin and to depress a ring of body tissue; an outer ring, the outer ring receiving the inner ring in a longitudinally slidable and relatively nonrotatable manner; and a retainer ring, the retainer ring receiving the guide tube in a longitudinally fixed and relatively nonrotatable manner, the retainer ring receiving the outer ring in a longitudinally slidable and relatively rotatable manner.

According to a further aspect, the present invention provides an arrangement of interfitting components for adjusting the penetration depth of a lancet and for stimulating an area surrounding an incision formed by penetration of a surface of the skin by the lancet, thereby facilitating the extraction of a sample of bodily fluid with a minimally invasive incision, the arrangement comprising a bottom end adapted to be applied to the surface of the skin, and a top end opposite the bottom end; a longitudinally moveable lancing member having a sharp end; a stop member setting a longitudinal travel distance of the lancing member; a bottom surface adapted to be applied to the surface of the skin, and an opening in the bottom surface through which the lancing member projects; a penetration depth defined by the distance between the end of the lancing device and the bottom surface; adjusting means for changing the penetration depth; and stimulation means for stimulating the area surrounding the incision and facilitating the extraction of the sample of bodily fluid.

BRIEF DESCRIPTION OF THE DRAWING FIGURES

FIG. 8A is a perspective view of a retainer ring according to the present invention;

FIG. 8B is a side view of the retainer ring of FIG. 8A;

FIG. 8C is a top end view of the retainer ring of FIG. 8A;

DETAILED DESCRIPTION OF THE INVENTION

Figure 1:
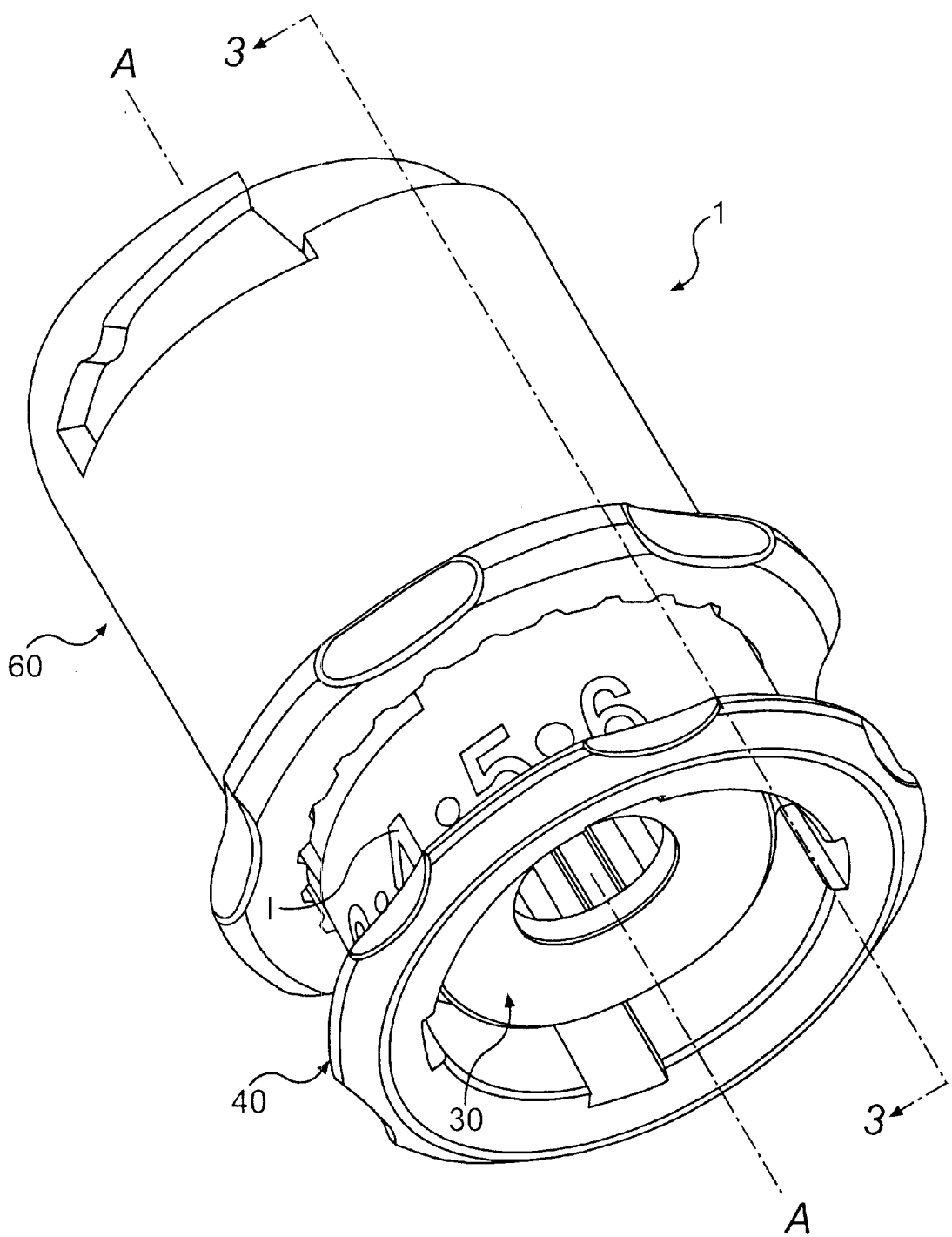
FIG. 1 is a perspective view of an adjustable assembly according to the principles of the present invention.
Figure 2:
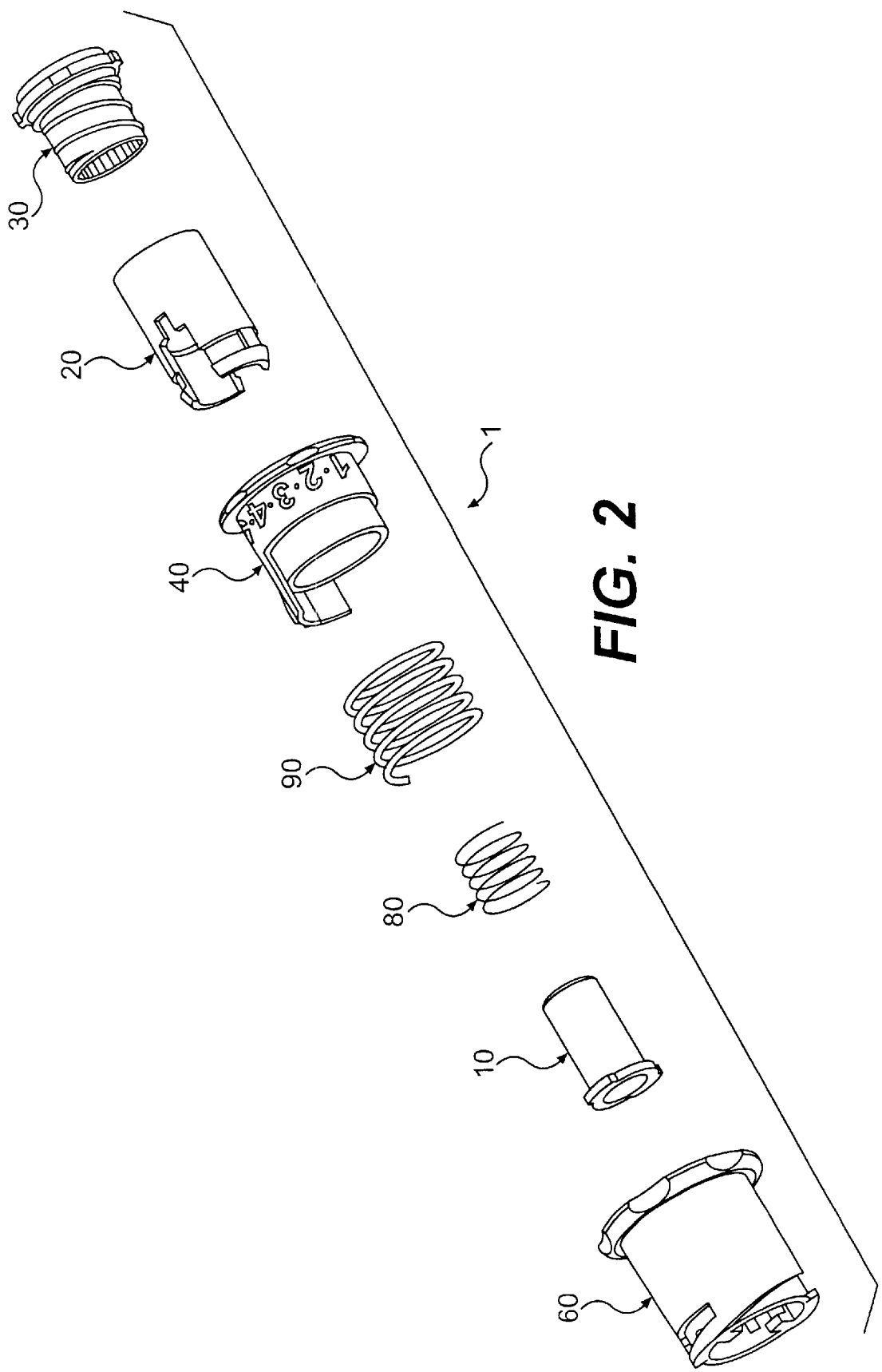
FIG. 2 is an exploded view of the adjustable assembly of FIG. 1.

The concepts of the present invention will now be further explained by reference to the following specific embodiments.

Before referencing the drawing figures, an overview of the construction, principles of operation, and method of the present invention is provided.

An adjustable assembly of the present invention includes a number of interfitting components. The adjustable assembly of the present invention is well-suited for adjusting the skin penetration depth of a lancing member when the assembly is used in conjunction with, or as a part of, a bodily fluid sampling device. Thus, the assembly can be formed as either a separate part that is attached or otherwise associated with a sampling device, or the assembly can be formed as an integral part of the overall sampling device.

The assembly carries an lancing member, such as a sharp lancet needle, that is constructed to pierce the skin surface, forming an incision therein from which a sample of bodily fluid can be extracted. The amount and makeup of the sample can be varied, depending upon penetration depth, location of sampling, amount of stimulation of the incision, etc.

The assembly has an end that is adapted to be applied to the surface of the skin. In the description that follows, this end will be referred to as the "bottom" end, and the opposite end will be referred to as the "top" end. The lancing member is driven or propelled toward the bottom end of the assembly, and ultimately into the surface of the skin. The travel distance of the lancing member within the assembly is preferably determined by a stop on one or more of the interfitting components.

One of the interfitting components includes a surface at the bottom end that is applied to the surface of the skin. This surface includes an opening through which the lancing member projects upon traveling within the assembly and engaging a stop member. Thus, the penetration depth is defined as the distance between the end of the lancing device or lancet and the above-mentioned surface which engages the skin.

This penetration depth can be altered by changing the separation distance between the stop member and the bottom surface of the component which engages the skin. When the separation between the stop member and the bottom surface is increased, the extent to which the lancet needle can protrude from the opening in the bottom surface is decreased (i.e.—decreasing the penetration depth). When the separation between the stop member and the bottom surface is decreased, the lancet needle can protrude further from the opening (i.e.—increasing the penetration depth).

The adjustable assembly further includes a stimulation means for stimulating the skin in the area surrounding the incision, thereby facilitating extraction of the sample of bodily fluid from the incision. Through this stimulation means, the desired sample can be extracted with a relatively small, and shallow minimally-invasive incision. The stimulation means can include one or more members constructed to engage and depress a ring of body tissue or skin in a manner which at least partially surrounds the incision. Preferably, at least one or more of the members is relatively moveable, at least in the longitudinal direction with respect to a housing of the sampling device.

FIGS. 1–8F illustrate, at least schematically, a preferred embodiment of an adjustable arrangement 1 of the present invention.

The adjustable arrangement 1 of the present invention is well-suited to be utilized in conjunction with a bodily fluid sampling device (not shown). It is envisioned that the arrangement of the present invention could be utilized with a number of different devices. By way of example, the arrangement is suited for use with samplers such as the ones disclosed in U.S. Pat. Nos. 5,879,311; 5,857,983; 6,048,352; 5,951,492; 5,951,493; 5,964,718, the disclosures of which are incorporated herein by reference. The adjustable arrangement can be in the form of a separate part that is attached to, or otherwise associated with, such a device (as in the illustrated embodiment). Alternatively, the arrangement could be formed integrally with the sampler to form a unitary device.

The adjustable arrangement 1 and one or more of its components can be formed from any suitable material. For example, the material could comprise a thermoplastic polymer. Moreover, one or more components of the adjustable assembly can be formed of a transparent or translucent material thereby enabling the user to observe the sampling procedure. This allows the user to visually determine whether a sample of bodily fluid has been extracted from the incision, without necessitating removal of the assembly from the surface of the skin to take it out of the line of sight.

An adjustable arrangement 1 according to the present invention comprises a number of interfitting components, as best illustrated in FIGS. 1–3B. The arrangement 1 generally includes a carrier 10 which is adapted to carry a lancet needle L or similar device. The carrier 10 is slidably received within a guide tube 20. An inner ring 30 is adjustably attached to the guide tube 20. The carrier 10, guide tube 20 and inner ring 30 are all received within an outer ring 40, which are received within a retainer, such as a retainer ring 60.

The inner ring 30 and the outer ring 40 cooperate such that there is no relative rotation between them. Thus by turning or rotating the outer ring 40 about the longitudinal axis A, the inner ring 30 is also rotated.

The carrier 10, guide tube 20, inner ring 30 and outer ring 40 are all received within a retainer ring 60. The outer ring 40 is rotatable within the retainer ring 60. In the illustrated embodiment, the arrangement 1 is constructed as a separate part for use in a sampling device (not shown). Thus the retainer ring 60 is to be affixed to the sampler device.

The top end of the guide tube 20 is mated with the top end of the retainer ring 60 in a nonrotatable manner such that the guide tube 20 cannot rotate relative to the retainer ring 60.

Figure 3A:
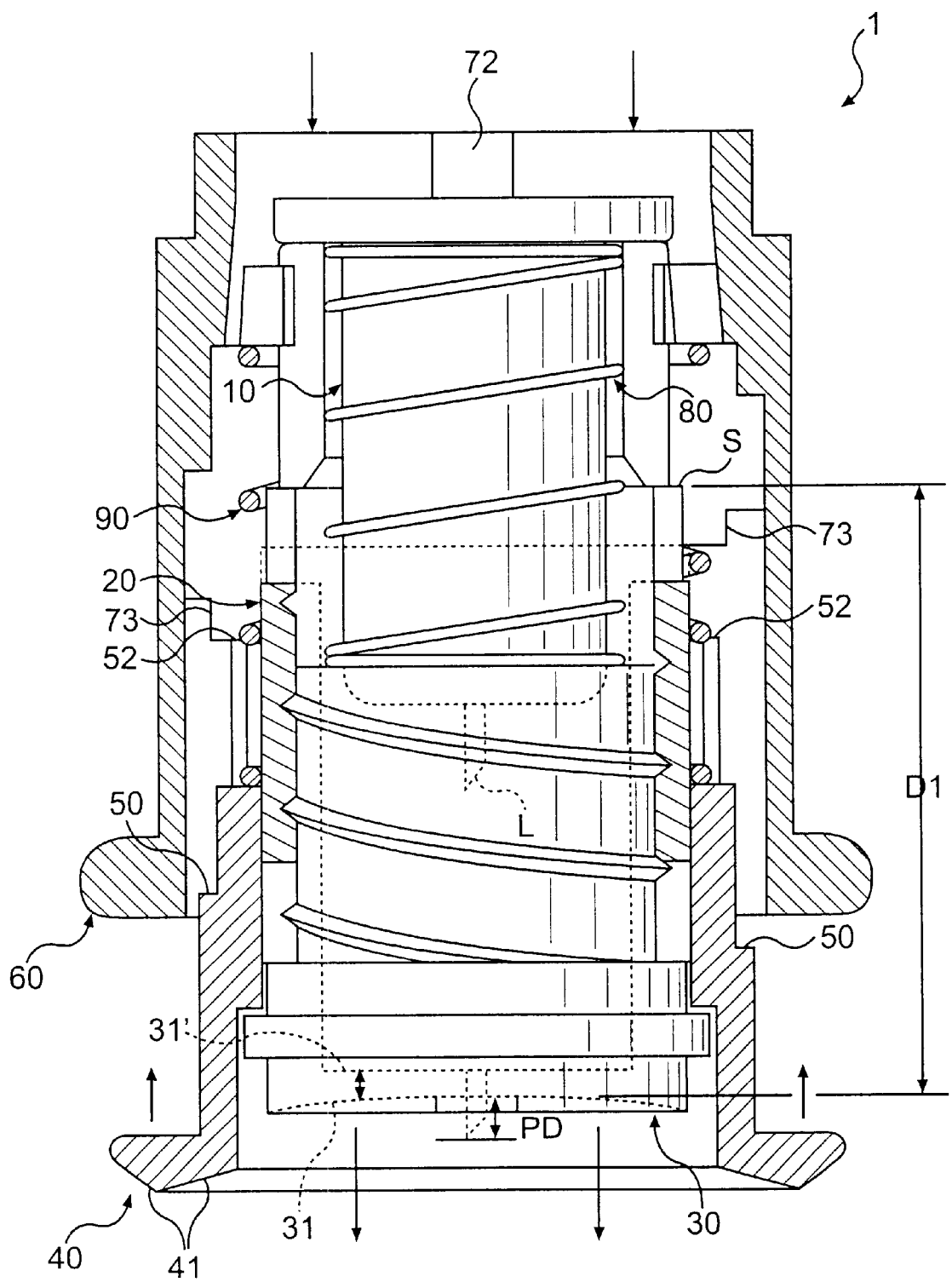
FIG. 3A is a cross-sectional view taken along line 3—3 of FIG. 1 showing the adjustable assembly at a first setting.
Figure 3B:
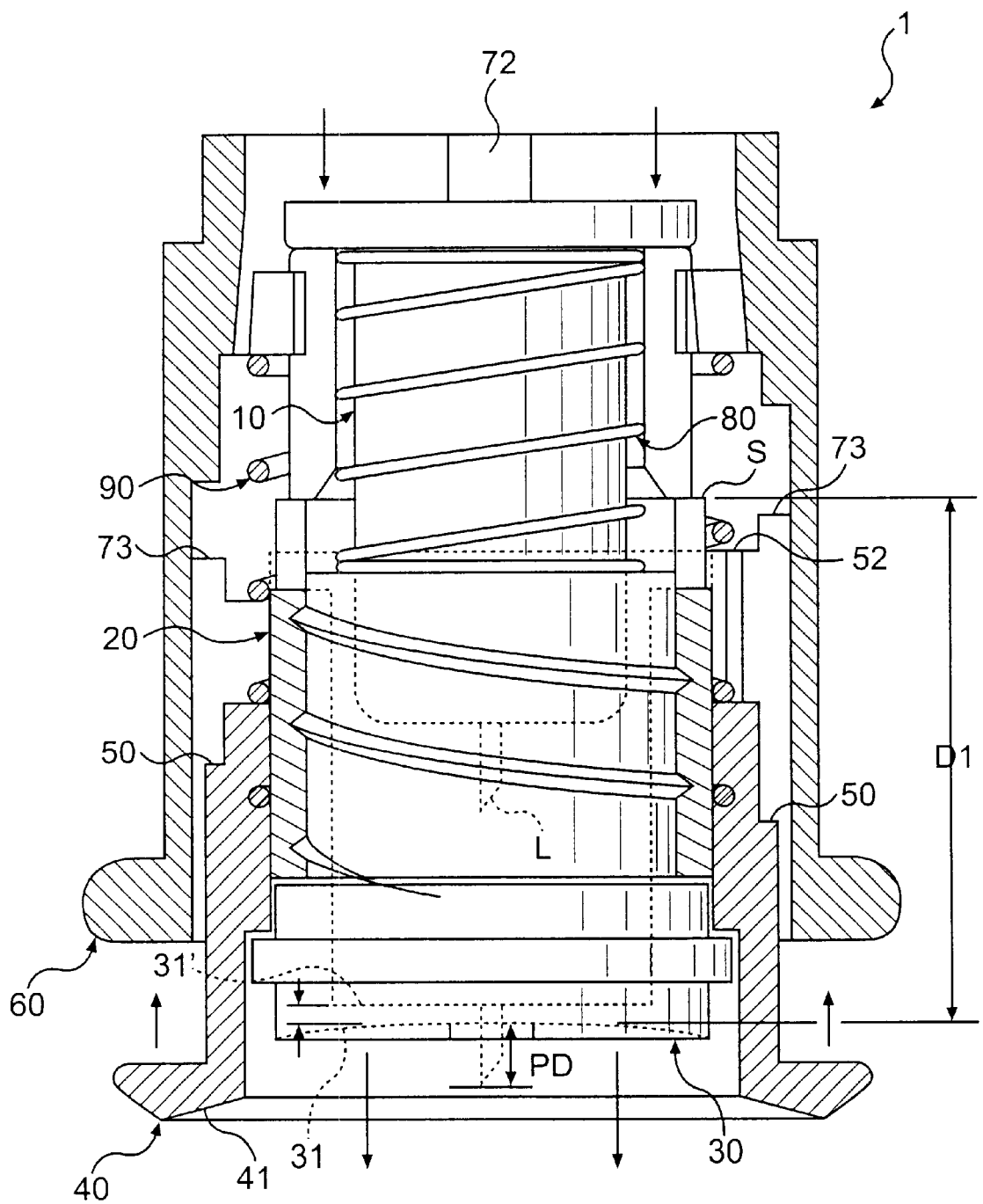
FIG. 3B is also a cross-sectional view taken along line 3—3 of FIG. 1 showing the adjustable assembly at a second setting.

Thus, when the outer ring 40 is rotated, the inner ring 30 rotates also. However, the guide tube 20 is prevented from being rotated via its connection to the retainer tube 60. This causes a relative rotation between guide tube 20 and the inner ring 30. As best illustrated in FIGS. 3A and 3B, according to one embodiment this rotation is used to alter the distance D1 between the stop member S and the bottom exterior surface 31 of the inner ring 30, thereby altering the penetration depth PD of the lancet L. Alternatively, the bottom of the carrier 10 may "bottom out" by coming into contact with the bottom interior surface 31' of the inner ring 30, in which case the surface 31' acts as a stop member.

The arrangement further includes means for stimulating the area of the incision formed in the skin surface by the lancet. Suitable stimulation means include mechanical, thermal, electromechanical, ultrasound, etc. Examples of suitable stimulation means can be found for example, in U.S. Pat. Nos. 5,951,493 and 5,964,718, the disclosures of which are incorporated herein by reference.

In the illustrated embodiment, at least the inner ring 30 and the outer ring 40 act as stimulator members. Upon application of the arrangement 1 to the surface of the skin, bottom surface 41 of the outer ring 40 first contacts the surface of the skin. As downward force is applied by the user, outer ring is forced back up into the retainer tube 60 under tension supplied by a biasing element 90. Simultaneously, inner ring 30 is advanced toward the skin until bottom surface 31 contacts the surface of the skin to depress ring of body tissue which surrounds the incision.

After the lancet has been driven into the surface of the skin, forming an incision therein, the user then applies a downward force onto the sampling device which is translated to the top of the arrangement 1 and directed downward. This force causes a ring of body tissue to be compressed in surrounding relationship to the incision, which causes the sides of incision to pull apart, thereby facilitating the extraction of the desired sample of bodily fluid. It is within the scope of the present invention that the pressure be applied once by the user. Alternatively, the user may release and reapply the pressure a number of times to effect a "pumping" or "milking" action, as described in detail, for example, in U.S. Pat. No. 5,951,493.

According to the above-described embodiment, at least one of the stimulation members is relatively moveable with respect to the retainer tube. However, it is within the scope of the present invention to make the stimulation members stationary with respect to the retainer tube.

While the above-mentioned components have been referred to as rings or tubes, it should be understood that it is within the scope of the present invention to provide such components with any suitable cross sectional shape, such as oval or polygonal. Moreover, the terms ring and tube are ones of convenience and should not be construed as limiting the geometry of dimensions of the components of the present invention.

The particular construction of individual components of the arrangement 1 will now be further described.

Figure 4A:
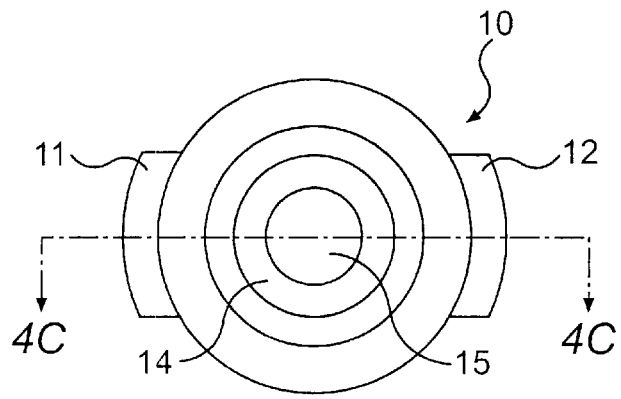
FIG. 4A is a top view of a lancet carrier according to the present invention.
Figure 4B:
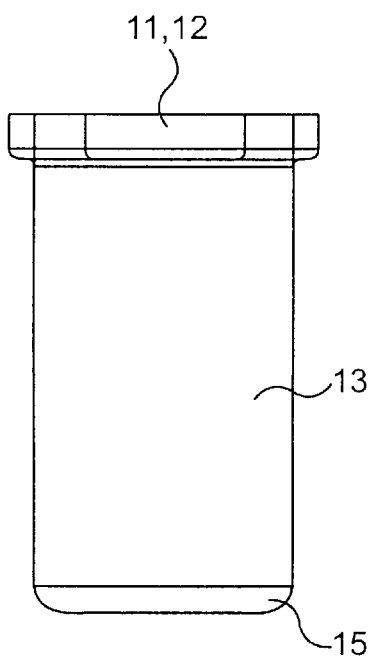
FIG. 4B is a side view of the lancet carrier of FIG. 4A.
Figure 4C:
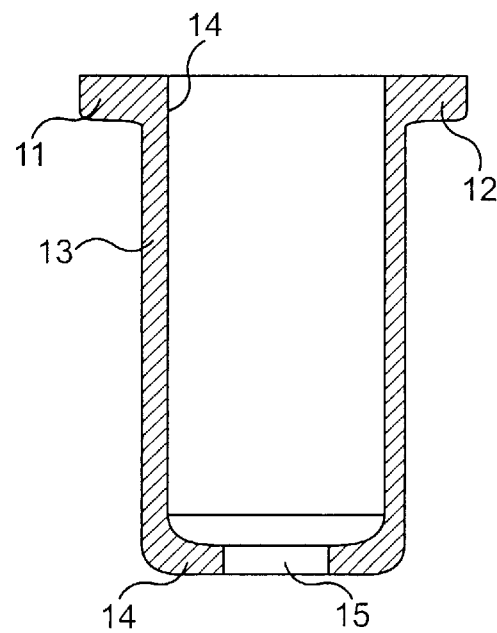
FIG. 4C is a cross-sectional view taken along line 4C—4C of FIG. 4A.

A carrier 10 constructed according to one preferred embodiment of the present invention is illustrated in FIGS. 4A–4C. However, the carrier 10 could have any suitable construction, so long as it performs its intended function. Namely, to securely hold a lancet L, receive and transmit a driving force from the associated sampling device, and to slidably travel within the assembly. In the illustrated embodiment, the carrier 10 includes one or more ears or projections 11, 12 at its top end. These projections 11, 12 are constructed to be slidably received by the guide tube 20. As a downward force is applied to the carrier, as indicated by the arrows appearing in FIGS. 3A and 3B, the carrier is forced downward within the guide tube 20 until the projections 11, 12 engage the stop member S of the guide tube 20, thereby defining a maximum travel length of the lancet carrier. The carrier 10 further includes an elongate body section 13, and bottom section 14 having a central opening 15 through which the lancet L projects (FIGS. 3A and 3B).

With regard to the lancet element L, a number of different types and styles of lancet can be utilized with the arrangement of the present invention. In fact, the lancet L can comprise any type of device capable of forming the desired incision in the surface of the skin. By way of example, the lancet L can comprise a metallic needle held in a molded plastic element. Alternatively, the lancet L can comprise multiple projections or barbs, and could be formed entirely of plastic.

Figure 5A:
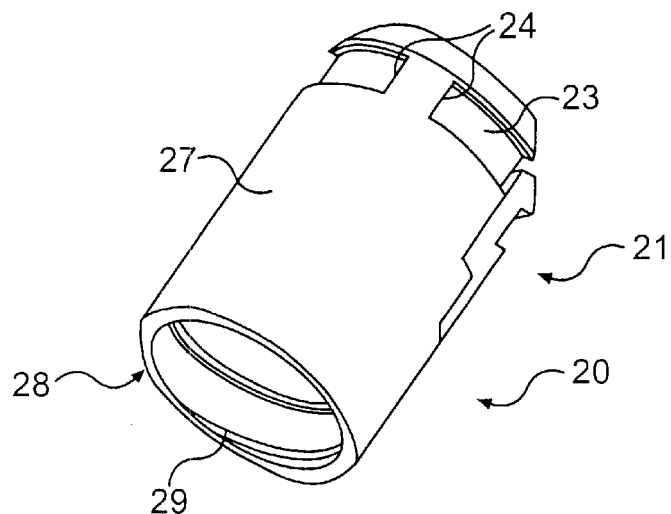
FIG. 5A is a perspective view of a guide tube according to the present invention.
Figure 5B:
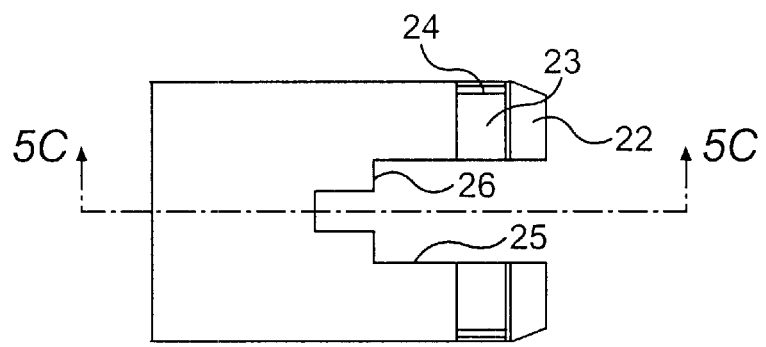
FIG. 5B is a side view of the guide tube of FIG. 5A.
Figure 5C:
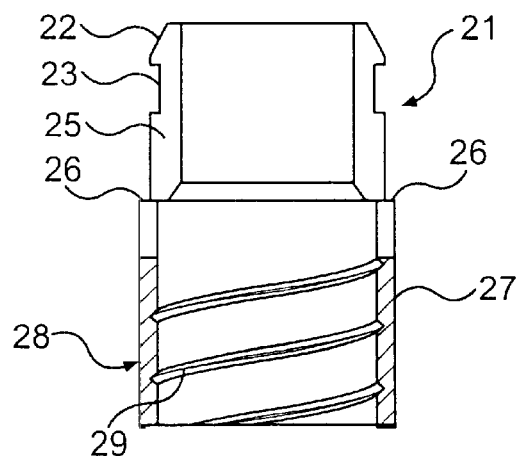
FIG. 5C is a cross-sectional view taken along line 5C—5C of FIG. 5B.

A guide tube 20 formed according to one embodiment of the present invention is illustrated in FIGS. 5A–5C. The guide tube 20 could have any suitable construction, so long as it performs its preferred function. Namely, that it be adjustably connectable to the inner ring 30, and that it be constructed to guide the movement of the carrier 10. In the illustrated embodiment, guide tube 20 comprises, starting at its top end, a retaining section 21 which is mated with, and retained by the retainer ring 60. The retaining section includes ramping surfaces 22 that facilitate insertion into the retainer ring 60, engagement slots 23 that mate with retaining projections disposed on the retainer ring 60, and anti-rotation stop surfaces 24 that prevent rotation of the guide tube 20 within the retainer ring 60. Guide slots 25 are provided at the top end of the guide tube 20 and extend longitudinally therefrom. Guide slots 25 are designed to slidably receive the projections 11, 12 of the carrier 10.

As previously noted, the arrangement of the present invention includes a stop member S which can limit the maximum travel length of the carrier 10 within the arrangement. This stop member could be constructed in a number of different ways, so long as the abovementioned function is performed. For example, the stop member S can comprise a stop surface, an interfitting mechanical engagement of two parts such as an interfitting projection and recess, or an wedging arrangement, etc. In the illustrated embodiment, the stop member S comprises a stop surface or shoulder 26 provided within the guide slots 25 of the guide tube 20. Thus, as illustrated in FIGS. 3A and 3B, carrier 10 is permitted to travel within guide slots 25 until projections 11, 12 of the carrier 10 engage the stop surfaces 26, which prevent further longitudinal movement of the carrier 10. Alternatively, depending upon the particular penetration depth setting, the bottom surface of carrier 10 may come into contact with the interior bottom surface 31' of the inner ring 30 before the projections 11, 12 engage the stop S of the guide tube 20.

The illustrated guide tube 20 further includes a cylindrical body section 27, and an adjustable connecting section 28.

The connecting section 28 can have any suitable construction that connects the guide tube 20 to the inner ring 30, and permits adjustment between these two components. In the illustrated embodiment, the connecting section comprises an internally threaded bore 29 that receives an externally threaded surface of the inner ring 30.

An inner ring 30 formed according to one embodiment of the present invention is illustrated in FIGS. 6A–6D. The inner ring can assume different constructions, so long as it performs its preferred function. Namely, that it be adjustably connectable to the inner ring 30, that it be constructed to guide the movement of the carrier 10, and that it is suitably constructed to act as a stimulator member. In the illustrated embodiment, the inner ring 30 comprises, starting from its bottom end, surface 31 which is adapted to contact the surface of the skin surrounding the incision. Preferably, surface 31 is beveled, forming an angle β of 10–65°, preferably 25–65°, thereby enhancing its ability to stimulate the incision. The beveled surface 31 is provided with an opening 32 through which the lancet L passes. Inner ring 30 further includes a retaining flange 33 which defines a longitudinal stop within the outer ring 40 when inserted therein.

The inner ring 30 also is provided with means to prevent relative rotation between the inner ring 30 and the outer ring 40, such that rotation of the outer ring 40 also causes rotation of the inner ring 30. A number of suitable constructions can be provided for this purpose. In the illustrated embodiment, flange 33 is provided with one or more antirotation tabs or projections 34, which are received in corresponding recesses disposed in the outer ring 40. This construction permits relative longitudinal movement between the inner ring 30 and the outer ring 40, but prevent relative rotation. An adjustable connecting section 35 is provided toward the top end of the inner ring 30. This connection section can have any suitable construction that permits and adjustable attachment between the inner ring 30 and the guide tube 20. In the illustrated embodiment, inner ring 30 is provided with external threads 36 that are configured to mate with the internal threads 29 of the guide tube 20. Thus, the top end of the inner ring is threaded into the bottom end of the guide tube 20.

Figure 6A:
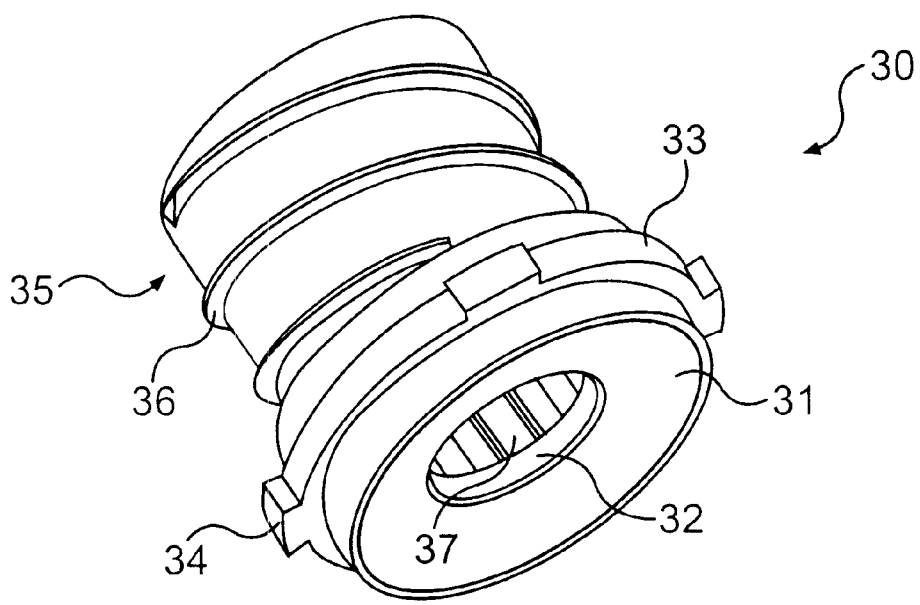
FIG. 6A is a perspective view of an inner ring according to the present invention.
Figure 6B:
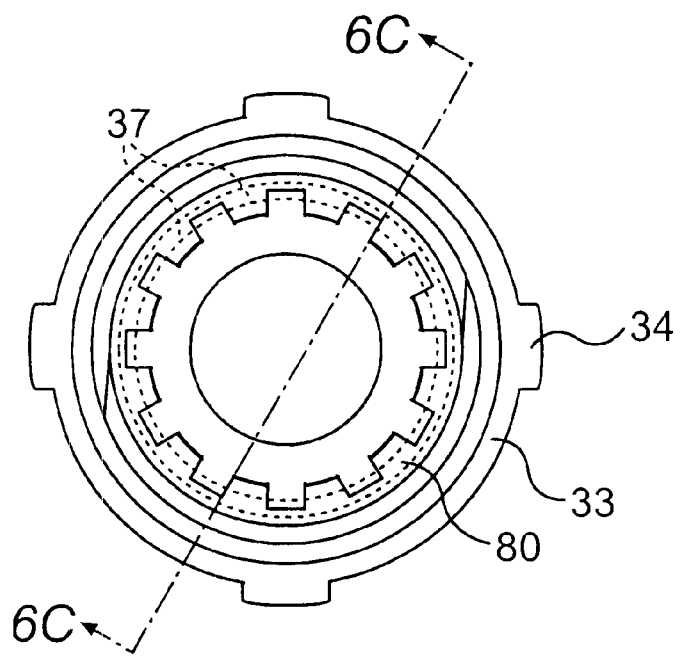
FIG. 6B is a top end view of the inner ring of FIG. 6A.
Figure 6C:
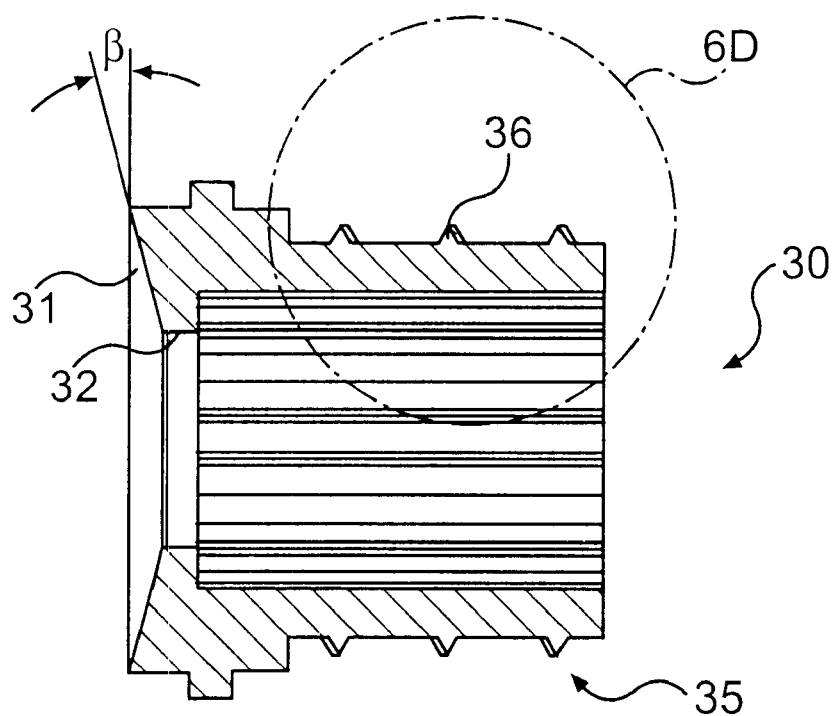
FIG. 6C is a cross-sectional view taken along lines 6C—6C of FIG. 6B.
Figure 6D:
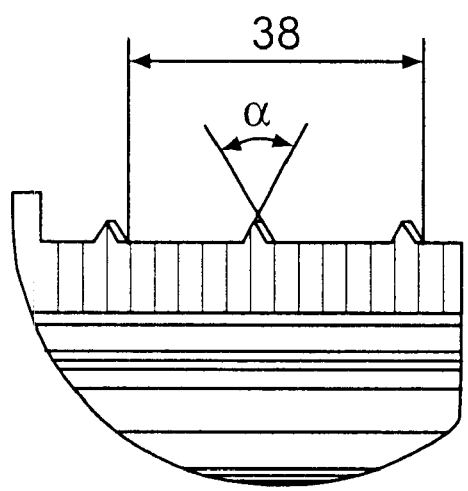
FIG. 6D is an enlarged view of area 6D as indicated in FIG. 6C.
Figure 7A:
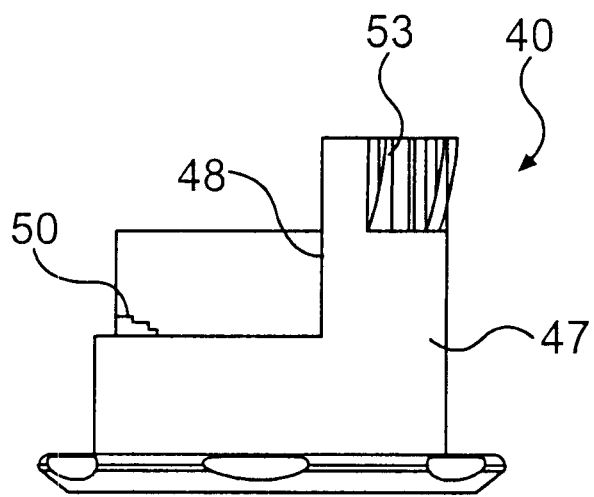
FIG. 7A is a side view of an outer ring according to the present invention.
Figure 7B:
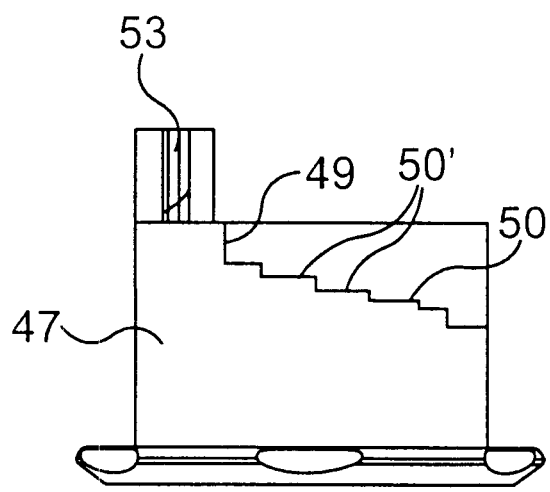
FIG. 7B is also a side view of the outer ring at a different orientation.
Figure 7C:
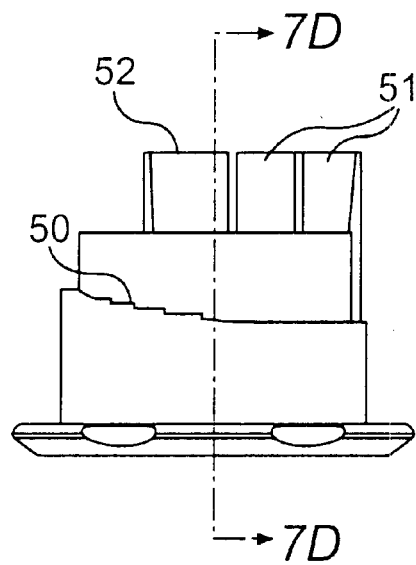
FIG. 7C is also a side view of the outer ring at yet another orientation.
Figure 7D:
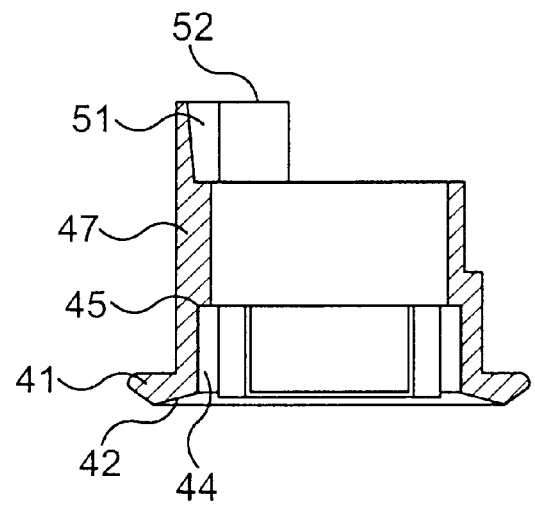
FIG. 7D is a cross-sectional view taken along line 7C—7C of FIG. 7B.
Figure 7E:
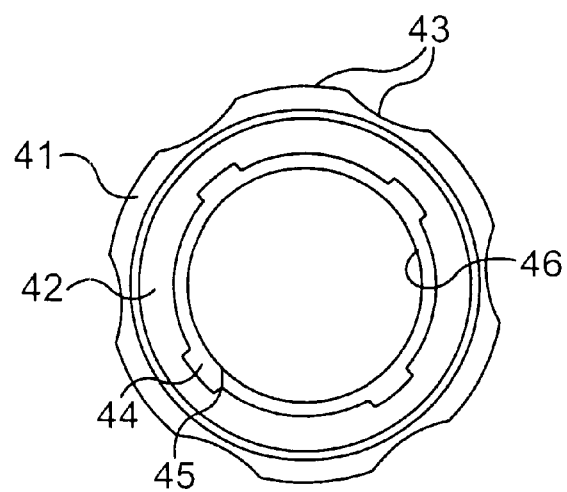
FIG. 7E is a bottom end view of the outer ring of FIG. 7A.
Figure 8D:
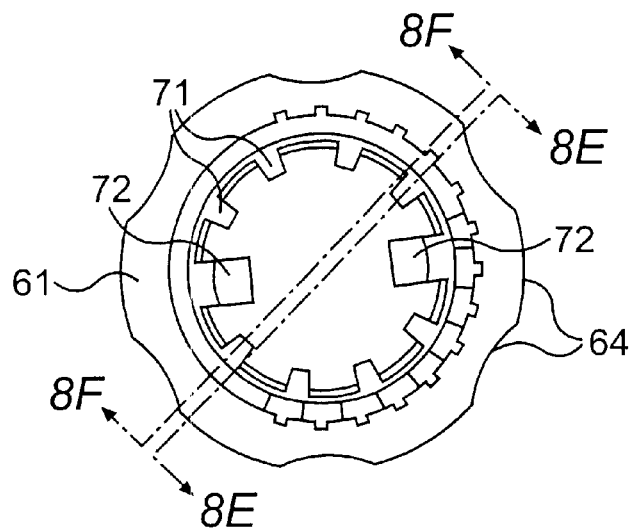
FIG. 8D is a bottom end view of the retainer ring of FIG. 8A.
Figure 8E:
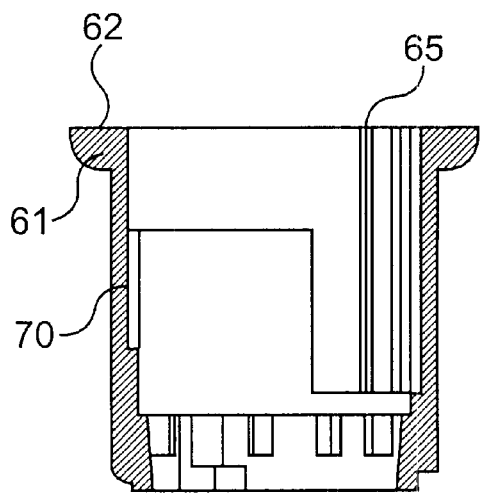
FIG. 8E is a cross-sectional view taken along line 8E—8E of FIG. 8D.
Figure 8F:
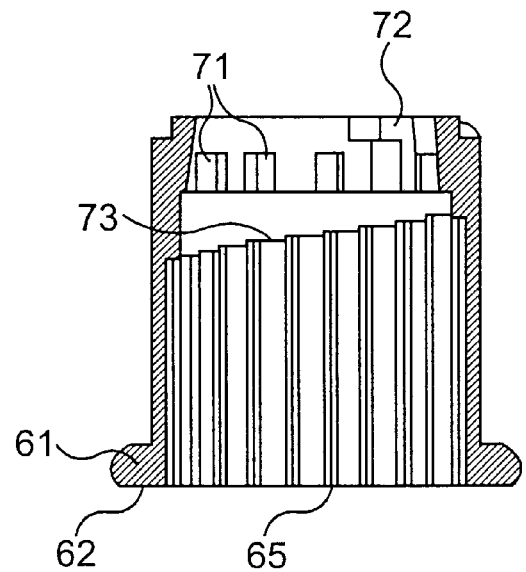
FIG. 8F is a cross-sectional view taken along line 8F—8F of FIG. 8D.

As best illustrated in FIGS. 6C and 6D, the mating threads are formed by teeth having contact faces forming and angle α, preferably, α is approximately 60°. The threads have a pitch 38 of about 0.240 inches. In an alternative embodiment, the pitch is about 0.300 inches. The threads on the inner ring are left handed in orientation.

In the illustrated embodiment, inner ring 30 further includes inwardly projecting longitudinal ridges 37 that perform a number of functions. For instance, ridges 37 act to add strength and structural integrity to the inner ring 30, act to guide the longitudinal movement of the carrier 10 which travels within the inner ring 30, and provide a platform at their top end upon which the lancet carrier biasing element 80 rests (FIG. 6B). Alternatively, the interior of the inner ring 30 can comprise a single diameter smooth bore.

An outer ring 40 formed according to one embodiment of the present invention is illustrated in FIGS. 7A–7E. The outer ring can assume different constructions, so long as it performs its preferred function. Namely, that it function, or assist in the function of stimulating the incision, receive the inner ring 30 in a longitudinally slidable, but nonrotatable manner, and interact with the retainer ring 60 such that the outer ring 40 is relatively rotatable and longitudinally moveable with respect to the retainer ring 60.

In the illustrated embodiment, outer ring 40 includes, starting from its bottom end, a bottom flange 41 having a bottom surface 42. Preferably, bottom surface 42 is beveled. The bottom surface 42 may be beveled at an angle of approximately 10–65°, preferably 25–65° so as to facilitate stimulation of the area surrounding the incision and to facilitate the overall operation of the device. Alternatively, bottom surface 42 may be provided with a different construction which achieves the same objective. Examples of suitable stimulator constructions are referenced above, and described in greater detail in U.S. Pat. No. 5,951,493.

The bottom flange 41 can be provided with a construction that facilitates grasping by the user. For instance, bottom flange 41 can be provided with alternating projections and grooves 43.

One or more longitudinally extending grooves 44 are provided, which extend from the bottom end of the outer ring 40. These grooves 44 receive antirotation projections 34 on the inner ring 30. The grooves 44 terminate in a stop shoulder 45 disposed inside of the outer ring 40. The stop shoulder limits the longitudinal movement of the inner ring 30 in the direction toward the top end of the outer ring 40, as illustrated, for example, in FIGS. 3A & 3B.

Outer ring 40 further includes an opening and inner bore 46.

An elongate body section 47 extends from the bottom flange 41. Body section 47 preferably includes indicia I (FIG. 1), disposed in a visible location which serve as an indication of the particular depth setting of the arrangement 1 of the overall device.

The outer ring 40 further includes a mechanism for limiting rotational movement within the retainer ring 60 over a predetermined range. A number of different constructions are possible to accomplish this objective. In the illustrated embodiment, the body section 47 includes a first stop surface 48 and a second stop surface 49. Stop surfaces 48 and 49 act to limit the rotation of the outer ring 40 within the retainer ring 60 over a predetermined range. Stop surfaces 48 and 49 a constructed to cooperate with corresponding stop surfaces on the interior of the retainer ring 60, thereby limiting rotation of the outer ring in both the clockwise and counterclockwise directions.

The adjustable arrangement 1 further comprises a mechanism for altering its longitudinal position relative to the retainer ring 60 in response to relative rotation between these two components. A number of constructions are possible to accomplish this function.

According to one embodiment, as illustrated in FIGS. 3A, 3B, 7A, 7B and 8F, at the top end of the body section 47, one or more flexible fingers or projections 51 are provided. These fingers 51 are rotatably and longitudinally slidably received within the retainer ring 60. The top surfaces 52 of the fingers 51 are constructed for engagement with a corresponding transition or stepped surface 73 disposed within the retainer ring 60. Thus, as the outer ring 40 is rotated, the top surfaces 52 of the fingers 51 will sequentially engage the longitudinally staggered surfaces 73. Fingers 51 can also be provided with ratcheting nubs 53 disposed on an exterior surface thereof. These nubs 53 are optionally constructed to be received within longitudinal grooves disposed in the interior of the retainer ring 60. As the outer ring 40 is rotated within the retainer ring 60, these nubs can jump from one longitudinal groove to an adjacent longitudinal groove upon application of a predetermined amount of rotational force by the user, thereby preventing unwanted rotation or an inadvertent change in the penetration depth setting of the arrangement 1. The abovementioned jumping of the nubs from groove to groove also provides an incremental ratcheting action to the rotational movement of the outer ring 40, which is beneficial to the precise operation of the device and may be appealing to the user.

The surface 50 is constructed to cooperate with a corresponding surface 73 on the retainer ring 60. Surface 50 can be formed in the manner of a staircase having ascending lands or "steps" 50'. As outer ring 40 is rotated within retainer ring 60, different steps 50' are brought to oppose the corresponding surface(s) 73 of the retainer ring 60. Thus, when the outer ring 40 is pushed longitudinally into the retainer ring 60, the steps 50' will eventually come into engagement with stepped surface 73 thereby providing a longitudinal stop to the retainer ring 40.

The retainer ring 60 formed according to one embodiment of the present invention is illustrated in FIGS. 8A–8F. The retainer ring can assume different constructions, so long as it performs its preferred function. For instance, that it fix the arrangement 1 to a sampling device, retain the guide tube 20, and slidably receives one or more components of the assembly, while permitting relative rotation.

As previously noted, the arrangement of the present invention can be formed as a separate part (as illustrated), or could be integrated into a sampling device. In the case where the arrangement forms an integral part of the sampling device, retainer ring 60 can comprise an integrated portion of the sampling device, instead of the separate ring of the illustrated embodiment. Thus, in the following description, the features mentioned below could be provided on a housing or other portion of a sampling device instead of on a separate ring of the arrangement.

In the illustrated embodiment, retainer ring 60 comprises, starting at its bottom end, a bottom flange 61. The bottom flange 61 includes a bottom surface 62, and an opening forming an inner bore 63. The bottom flange 61 may be provided with grasping formations, such as alternating projections and recesses 64.

An indicator or pointer R may be provided on bottom flange 61, which cooperates with the indicia I on the outer ring 40 to indicate and identify the particular setting of the adjustable arrangement 1.

The inner bore 63 includes longitudinally extending grooves 65 that are constructed to receive the ratcheting nubs 53 of the fingers 51 on the outer ring 40, in the manner previously described.

The inner bore 63 further comprises a land 66 constructed to cooperate with the outer ring 40 in the following manner. Land 66 comprises first and second stop surfaces 67 and 68 that are constructed to limiting the amount of relative rotation between the outer ring 40 and the retainer ring 60 in both the clockwise and counterclockwise directions. The land 66 further includes surface 69 which can cooperate with the transition surface 50 of the outer ring 40 to provide a longitudinal stop for the outer ring 40 as described above.

An elongate body section 70 extends from the bottom flange 61.

A plurality of retainer projections 71 extend from the inner bore 63. These projections are constructed to mate with the engagement slots 23 provided on the guide tube 20, thereby positively retaining and longitudinally locking the guide tube 20 within the retainer ring 60. A pair of adjacent projections 71 receive guide tube antirotation stop surfaces 24 therebetween. Thus, guide tube 20 is also prevented from relative rotation within retainer ring 60 by projections 71. It should be noted that other retaining arrangements are contemplated. For instance, instead of projections 71, an annular rib could be provided on the retainer ring 60, with recess that mate with the guide tube 20.

One or more retention tabs 72 are further provided at the top end portion of the retainer ring 60. Retention tabs 72 are constructed to project inwardly by a sufficient amount so as to overlie and longitudinally retain projections or flanges 11 and 12 of the carrier 10 underneath them.

An attachment feature may be provided at the outer periphery of the top end of retainer ring 50 for connecting the arrangement 1 to a suitable sampling device. According to the illustrated embodiment, attachment 73 comprises a groove 74 with locking bump 75 for receiving an mating projection (not shown).

The arrangement of the illustrated embodiment of the present invention further includes biasing elements 80 and 90. While biasing elements 80 and 90 are shown as coil springs in the illustrated embodiment, it should be understood that the biasing elements 80 and 90 can take other forms such as leaf springs, stacked Belville washers, and/or an elastomeric element.

Biasing element 80 fits over the carrier 10 and is retained under projections 11 and 12 of the carrier 10. The opposite end of the biasing element 80 rests upon the end of the inner ring 30. According to a preferred embodiment, the inwardly projecting longitudinal ridges 37 act as a seat for the bottom end of biasing element 80. Biasing element 80 functions to provide a return force for the lancet carrier 10 and the lancet needle L disposed therein. Thus, after the downward force represented by the arrows shown in FIGS. 3A and 3B has been removed, and after the lancet L has penetrated the surface of the skin to form an appropriate incision therein, biasing element 80 provides a return force that drives the carrier 10 and lancet L back into the arrangement 1 so that the end of lancet L is no longer exposed.

One end of biasing element 90 rests on the top surface of the body section 47 of the outer ring 40. The opposite or top end of the biasing element 90 is retained under retaining projections 71 of the retainer ring 60. The biasing element 90 provides a reaction force in response to upward movement of the outer ring 40 indicated by the arrows appearing in FIGS. 3A and 3B. This construction facilitates stimulation of the area surrounding the incision thereby aiding in the extraction of an adequate sample of bodily fluid.

An arrangement constructed according to the present invention provides several important advantages. For instance, the arrangement provides a relatively simple construction which enables accurate and reliable adjustment of the penetration depth of a bodily fluid sampling device thereby enhancing the user's ability to obtain an adequate sample with a minimally invasive incision. Moreover, operation of the arrangement has a pleasing "feel" and appearance to the user, thereby reducing the apprehension associated with the use of such devices. Importantly, the arrangement further incorporates a stimulation feature which enables the adjustable arrangement to extract an adequately-sized sample of bodily fluid from the incision, from a minimally invasive incision thereby further reducing pain associated with such testing procedures.

While the present invention has been described by reference to the above-mentioned embodiments, certain modifications and variations will be evident to those of ordinary skill in the art. Therefore, the present invention is to limited only by the scope and spirit of the appended claims.

We claim:

1. An adjustable arrangement, comprising:

a carrier;

a guide tube, the guide tube receiving the carrier in a longitudinally slidable manner, the guide tube comprises a stop member limiting longitudinal movement of the carrier;

an inner ring, the inner ring adjustably attached to the guide tube, the inner ring comprising a bottom surface adapted to contact a surface of the skin and to depress a ring of body tissue;

an outer ring, the outer ring receiving the inner ring in a longitudinally slidable and relatively nonrotatable manner;

a retainer ring, the retainer ring receiving the guide tube in a longitudinally fixed and relatively nonrotatable manner, the retainer ring receiving the outer ring in a longitudinally slidable and relatively rotatable manner; and wherein the guide tube further comprises a top end comprising a retaining section; a plurality of guide slots extending longitudinally from the top end, each guide slot comprising a stop surface; a body section; and connecting section comprising an internally threaded bore.

2. The arrangement of claim 1, wherein the bottom surface of the inner ring is beveled at an angle of 10 to 65°.

3. The arrangement of claim 1, further comprising a lancet received within the carrier.

4. The arrangement of claim 1, wherein the carrier further comprises a top end having one or more projections, an elongate body section, and a bottom section having a central opening.

5. An adjustable arrangement, comprising:

a carrier;

a guide tube, the guide tube receiving the carrier in a longitudinally slidable manner, the guide tube comprises a stop member limiting longitudinal movement of the carrier;

an inner ring, the inner ring adjustably attached to the guide tube, the inner ring comprising a bottom surface adapted to contact a surface of the skin and to depress a ring of body tissue;

an outer ring, the outer ring receiving the inner ring in a longitudinally slidable and relatively nonrotatable manner;

a retainer ring, the retainer ring receiving the guide tube in a longitudinally fixed and relatively nonrotatable manner, the retainer ring receiving the outer ring in a longitudinally slidable and relatively rotatable manner; and wherein the inner ring further comprises an opening disposed in the bottom end; a retaining flange forming a longitudinal stop with respect to the outer ring, and one or more antirotation projections; a plurality of internal longitudinally extending ridges receiving the carrier therein; and a connecting section comprising external threads constructed to mate with the internal threads of the guide tube.

6. The arrangement of claim 5, wherein the outer ring further comprises a bottom surface adapted to contact a surface of the skin; one or more longitudinally extending grooves terminating in a stop shoulder receiving the one or more antirotation projections of the inner ring; first and second stop surfaces limiting rotational movement of the outer ring with respect to the retainer ring; and a transition surface between the stop surfaces for limiting the longitudinal movement of the outer ring within the retainer ring.

7. The arrangement of claim 6, wherein the outer ring further comprises a bottom flange having alternating projections and grooves.

8. The arrangement of claim 6, wherein the outer ring further comprises a body section provided with indicia.

9. The arrangement of claim 6, wherein the transition surface comprises a plurality of steps.

10. The arrangement of claim 6, wherein the outer ring further comprises a body section and one or more flexible fingers extending from a top portion of the body section.

11. The arrangement of claim 6, wherein:

the outer ring includes indicia; and the retainer ring further comprises a bottom flange comprising a pointer for cooperation with the indicia of the outer ring.

12. An adjustable arrangement, comprising:

a carrier;

a guide tube, the guide tube receiving the carrier in a longitudinally slidable manner, the guide tube comprises a stop member limiting longitudinal movement of the carrier;

an inner ring, the inner ring adjustably attached to the guide tube, the inner ring comprising a bottom surface adapted to contact a surface of the skin and to depress a ring of body tissue;

an outer ring, the outer ring receiving the inner ring in a longitudinally slidable and relatively nonrotatable manner;

a retainer ring, the retainer ring receiving the guide tube in a longitudinally fixed and relatively nonrotatable manner, the retainer ring receiving the outer ring in a longitudinally slidable and relatively rotatable manner; and wherein retainer ring further comprises an inner bore comprising a land having first and second stop surfaces; an elongate body section; a plurality of retainer projections extending from a top end of the inner bore receiving a portion of the guide tube; one or more retention tabs disposed at the top end of the retainer ring overlying at least a portion of the carrier; and an attachment formation.

13. An adjustable arrangement comprising:

a carrier;

a guide tube, the guide tube receiving the carrier in a longitudinally slidable manner, the guide tube comprises a stop member limiting longitudinal movement of the carrier;

an inner ring, the inner ring adjustably attached to the guide tube, the inner ring comprising a bottom surface adapted to contact a surface of the skin and to depress a ring of body tissue;

an outer ring, the outer ring receiving the inner ring in a longitudinally slidable and relatively nonrotatable manner;

a retainer ring, the retainer ring receiving the guide tube in a longitudinally fixed and relatively nonrotatable manner, the retainer ring receiving the outer ring in a longitudinally slidable and relatively rotatable manner; and a first biasing element disposed over the carrier, the first biasing element retained between projections disposed on a top end of the carrier and a top surface of the inner ring; and second biasing element, the second biasing element being retained between a top surface of the body section of the outer ring and retaining projections disposed on the retainer ring.

14. The arrangement of claim 13, wherein the first and second biasing elements comprise coil springs.

15. An arrangement of interfitting components for adjusting the penetration depth of a lancet and for stimulating an area surrounding an incision formed by penetration of a surface of the skin by the lancet, thereby facilitating the extraction of a sample of bodily fluid with a minimally invasive incision, the arrangement comprising;

a bottom end adapted to be applied to the surface of the skin, and a top end opposite the bottom end;

a longitudinally moveable lancing member having a sharp end;

a stop member setting a longitudinal travel distance of the lancing member;

a bottom surface adapted to be applied to the surface of the skin, and an opening in the bottom surface through which the lancing member projects; a penetration depth defined by the distance between the end of the lancing device and the bottom surface;

adjusting means for changing the penetration depth;

stimulation means for stimulating the area surrounding the incision and facilitating the extraction of the sample of bodily fluid;

wherein the stimulation means comprises one or more stimulating members constructed to depress a ring of body tissue in a manner which at least partially surrounds the incision; and wherein the components of the arrangement comprise an outermost ring member concentrically surrounding the other components, and at least one of the stimulating members is longitudinally moveable with respect to the outermost ring member.

16. The arrangement of claim 15, wherein the stimulation means comprises a beveled surface.

17. The arrangement of claim 15, wherein the adjusting means comprises means for changing a separation distance defined between the stop member and the bottom surface in response to relative rotation between two or more components of the arrangement.

18. An apparatus, comprising:

a retainer;

a guide coupled to the retainer in a non-rotatable manner to minimize relative rotation between the retainer and the guide, the guide having a stop member;

a carrier slidably received in the guide tube, the retainer being configured to carry a lancet for lancing skin, the carrier having a portion configured to contact the stop member of the guide to limit penetration depth of the lancet into the skin;

an inner member defining an opening through which the lancet extends to lance the skin, the inner member having a skin-contacting surface surrounding the opening that is adapted to contact the skin, the inner member being threadedly engaged with the guide for adjusting a distance between the stop member and the skin-contacting surface in order to adjust the penetration depth of the lancet; and an outer member slidably received around the inner member, the outer member having a skin-engaging surface adapted to engage the skin for expressing fluid from an incision formed by the lancet.

19. The apparatus of claim 15, wherein:

the inner member has an antirotation tab; and the outer member defines a longitudinal groove in which the tab is slidably received to minimize relative rotation between the inner member and the outer member while permitting relative longitudinal movement between the inner member and the outer member.

20. The apparatus of claim 19, further comprising a biasing element positioned between the retainer and the outer member to bias the outer member against the skin.

21. The apparatus of claim 18, further comprising a biasing element positioned between the retainer and the outer member to bias the outer member against the skin.

22. The apparatus of claim 21, further comprising a second biasing element positioned between the carrier and the inner member to retract the lancet after lancing the skin.

23. The apparatus of claim 21, wherein the biasing element includes a coil spring.

24. The apparatus of claim 18, further comprising the lancet.

25. The apparatus of claim 18, wherein the inner member and the outer member are ring-shaped.

26. The apparatus of claim 25, wherein the retainer and the outer member each have staircase-shaped surfaces to limit longitudinal movement of the outer member.

* * * * *